United States Patent
Bartz et al.

(10) Patent No.: US 9,687,601 B2
(45) Date of Patent: Jun. 27, 2017

(54) TOOL FOR INTERFACING WITH AN INFUSION PUMP

(75) Inventors: Troy A. Bartz, Lake Orion, MI (US); Paul T Kotnik, Commerce Township, MI (US); Rana Balci, Troy, MI (US); Rajat Khare, Bangalore (IN)

(73) Assignee: Curlin Medical Inc., East Aurora, NY (US)

( * ) Notice: Subject to any disclaimer, the term of this patent is extended or adjusted under 35 U.S.C. 154(b) by 675 days.

(21) Appl. No.: 13/127,527

(22) PCT Filed: Oct. 22, 2009

(86) PCT No.: PCT/US2009/061582
§ 371 (c)(1),
(2), (4) Date: Jul. 13, 2011

(87) PCT Pub. No.: WO2010/053704
PCT Pub. Date: May 14, 2010

(65) Prior Publication Data
US 2011/0264044 A1 Oct. 27, 2011

Related U.S. Application Data

(60) Provisional application No. 61/198,853, filed on Nov. 10, 2008.

(51) Int. Cl.
*A61M 5/142* (2006.01)
*A61M 5/145* (2006.01)
*G06F 19/00* (2011.01)

(52) U.S. Cl.
CPC ........ *A61M 5/14212* (2013.01); *A61M 5/145* (2013.01); *G06F 19/326* (2013.01); *G06F 19/3468* (2013.01); *A61M 5/14228* (2013.01); *A61M 5/14232* (2013.01); *A61M 2205/3561* (2013.01); *A61M 2205/3592* (2013.01); *A61M 2205/6009* (2013.01); *A61M 2205/6018* (2013.01); *A61M 2205/6072* (2013.01)

(58) Field of Classification Search
CPC ... A61M 2205/6072; A61M 2205/6009; G06F 19/326; G06F 19/3468
USPC ................ 604/65–67; 700/87, 282; 705/2, 3
See application file for complete search history.

(56) References Cited

U.S. PATENT DOCUMENTS

| | | | |
|---|---|---|---|
| 6,269,340 B1 * | 7/2001 | Ford et al. | .......................... 705/3 |
| 6,640,246 B1 * | 10/2003 | Gary, Jr. | ............... G06F 19/327 709/223 |
| 2003/0140929 A1 * | 7/2003 | Wilkes et al. | ................. 128/898 |
| 2003/0197062 A1 | 10/2003 | Shaw | |
| 2005/0144043 A1 * | 6/2005 | Holland et al. | .................... 705/3 |
| 2005/0283210 A1 * | 12/2005 | Blischak | ........... A61M 5/14276 607/60 |
| 2006/0265246 A1 * | 11/2006 | Hoag | ............................... 705/2 |
| 2007/0213598 A1 * | 9/2007 | Howard et al. | ............... 600/300 |

(Continued)

FOREIGN PATENT DOCUMENTS

WO   2005036447   4/2005

*Primary Examiner* — Matthew F Desanto
(74) *Attorney, Agent, or Firm* — Hodgson Russ LLP

(57) ABSTRACT

A tool or computer-readable medium for interfacing with an infusion pump includes i) computer-readable code for generating a drug library, generating a run profile, or a combination thereof, and ii) computer-readable code for configuring the infusion pump.

12 Claims, 2 Drawing Sheets

(56) References Cited

U.S. PATENT DOCUMENTS

2007/0233035 A1 10/2007 Wehba et al.
2008/0034323 A1* 2/2008 Blomquist .................... 715/810

* cited by examiner

TOOL FOR INTERFACING WITH AN INFUSION PUMP

CROSS REFERENCE TO RELATED APPLICATION

This application claims the benefit of U.S. Provisional Patent Application Ser. No. 61/198,853 for a TOOL FOR INTERFACING WITH AN INFUSION PUMP, filed on Nov. 10, 2008, which is hereby incorporated by reference in its entirety. This claim is made under 35 U.S.C. §119(e); 37 C.F.R. §1.78; and 65 Fed. Reg. 50093.

TECHNICAL FIELD OF INVENTION

The pres ent disclosure relates generally to infusion pumps and, more particularly, to a tool for interfacing with an infusion pump.

BACKGROUND

Infusion pumps are often used to deliver fluid in a controlled manner such as, for example, an intravenous delivery of pharmaceutical compositions (i.e., a drug) to a patient or subject. In some instances, the infusion pump may be programmable with an infusion protocol for delivering the drug to the subject. The infusion protocol, which may, for example, include a name of a drug, a dosage of the drug, and a mode of delivering the drug to the patient, is sometimes checked against pre-established safety standards, which may be saved in a master drug library.

SUMMARY

A tool or computer-readable medium for interfacing with an infusion pump includes i) computer-readable code for generating a drug library, generating a run profile, or a combination thereof, and ii) computer-readable code for configuring the infusion pump.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION

A tool for interfacing with an infusion pump (referred to herein as a main tool) is a computer-readable medium integrating at least two different tools together. In an embodiment, the main tool includes i) a tool for generating a drug library and/or for generating a run profile (referred to herein as a pharmacy tool) and ii) a tool for configuring the infusion pump (referred to herein as a biotech tool). In another embodiment, the main tool includes i) the pharmacy tool, ii) the biotech tool, and iii) a tool for configuring the main tool for a user. The main tool, which is used on a computer remote from the infusion pump, is advantageously user-friendly and is compatible with and/or may be used on a number of different computer systems. Further, the main tool may advantageously be used for interfacing with a plurality of pumps.

Figure 1:
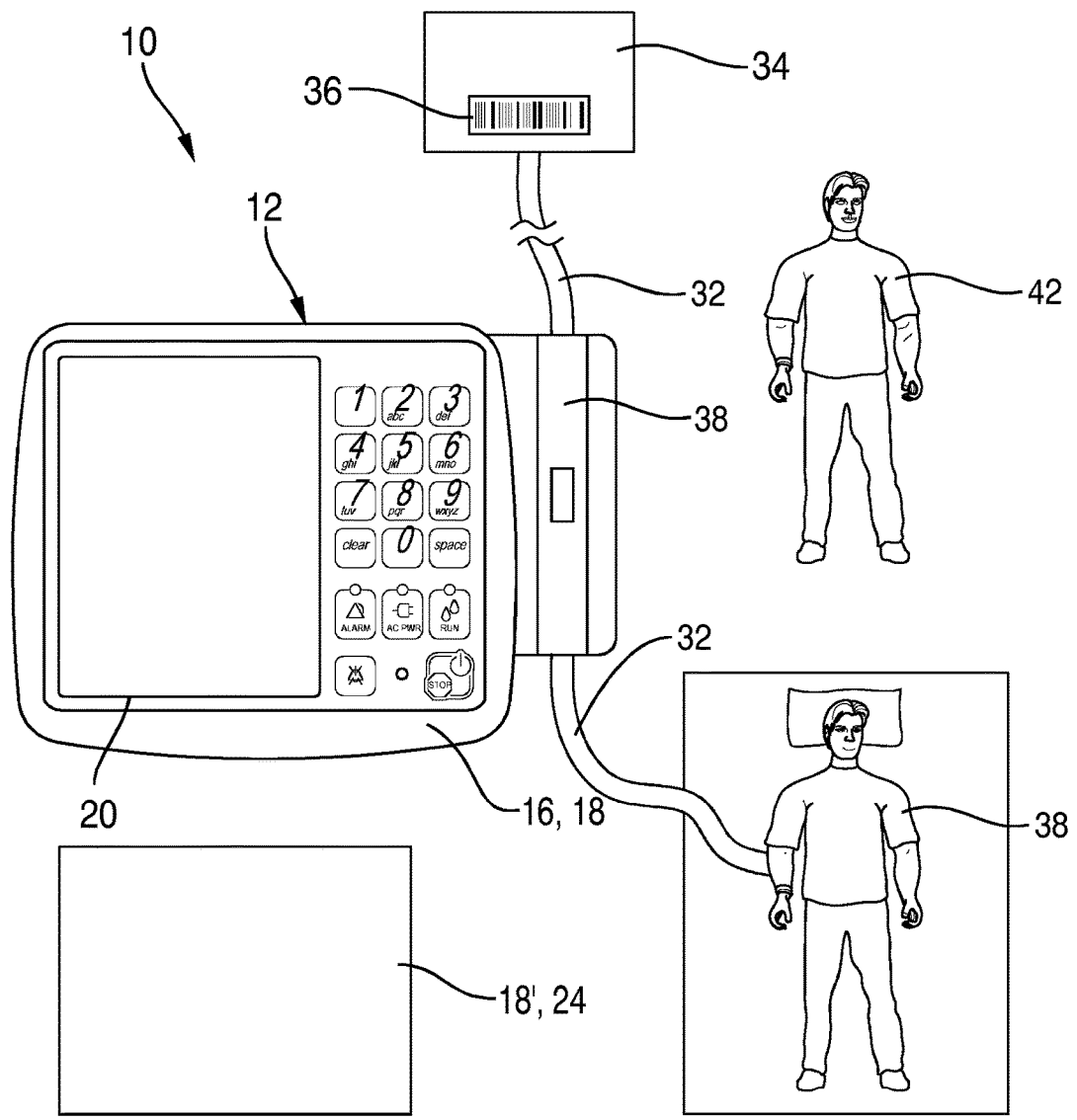
FIG. 1 is a semi-schematic depiction of an example of an infusion pump system.

An example of an infusion pump system 10 that may be used for embodiment(s) of the method disclosed herein is semi-schematically depicted in FIG. 1. The infusion pump system 10 includes an infusion pump 12, such as a rotary peristaltic pump as shown in FIG. 1. Such rotary peristaltic infusion pumps may include a removable cassette 30 including an assembly of rollers (not shown) and a flexible tube 32 that surrounds a portion of the assembly of rollers. In response to rotational movement of the rollers, portions of the flexible tube 32 in contact with the rollers compress or otherwise occlude against a wall of the cassette 30. As a result, fluid (i.e., a drug) traveling through the tube 32 is temporarily trapped in the tube 32 between the occluded points. The trapped drug is released from the tube 32 when the occlusion force on the tube 32 is released. In this manner, the drug is urged through the tube 32 via peristaltic wave action and is ultimately delivered to a patient or subject 38.

While a rotary peristaltic pump is shown and described herein, it is to be understood, that other infusion pumps are also suitable for use in the methods of the present disclosure Examples of such other infusion pumps include syringe pumps and linear peristaltic pumps.

The infusion pump 12 also includes a user interface 16 operatively connected thereto. The user interface 16 includes a data entry system 18 for inputting data related to, for example, a drug, a subject 38, a caregiver 42, and/or a protocol for infusing the drug to the subject 38. In one example, the data entry system 18 is a twelve-digit keypad, operatively associated with a display 20, which together enable manual entry of the data. The display 20 may, in an example, be a standard display exhibiting black-and-white and/or color graphic and alpha-numeric characters. The display 20 may, in another example, be a color touch screen.

In some cases, the display 20 may further include an ambient light detection feature (not shown) to determine how optically bright the ambient environment is. The light detection feature may automatically adjust the backlighting of the display 20 depending, at least in part, on increased or decreased lighting of the ambient environment. Further, the display 20 may include a dimming feature, where the optical brightness of the display 20 dims when the infusion pump 12 is continuously operated at substantially the same setting(s).

In another example, the data entry system 18' is a machine-readable scanner 24 operatively associated with the infusion pump 12. In some instances, the machine-readable scanner 24 communicates with the infusion pump 12 via a wired connection. In other instances, the machine-readable scanner 24 communicates with the infusion pump 12 via a wireless connection. In these instances, the machine-readable scanner 24 wirelessly transmits the data to the infusion pump 12, and the infusion pump 12 receives the data via a receiver R operatively connected to the user interface 16.

In an example, the machine-readable scanner 24 is a barcode scanner configured to read barcode labels having information stored thereon. In some cases, a barcode label may be associated with a subject or patient 38 and include data such as the subject's name and personal information related to the subject 38 (e.g., allergies, current health status, etc.). Another barcode label may be associated with the caregiver 42 and include data such as the caregiver's name and other relevant identification information related to the caregiver 42. Yet another barcode label (shown as reference numeral 36 in FIG. 1) may be associated with a drug container 34 and include data such as a drug name, data associated with the drug corresponding to the drug name, and a protocol for infusing the drug to the subject 38. The data included in any of the barcode labels described above may be used to program the infusion pump 12 and/or verify that the recipient of the drug to be infused is accurate, which is described in further detail in U.S. Patent Provisional Application Ser. No. 61/198,681, the disclosure of which is herein incorporated by reference in its entirety.

The user interface 16 further includes a processor P operatively associated with the display 20 and the data entry system 18. The processor P has stored therein a program for, e.g., inputting data into the infusion pump 12 for programming the pump 12 for a particular infusion. Further details of examples of inputting data into the infusion pump 12 is described in commonly-owed U.S. Patent Provisional Application Ser. No. 61/198,817, which is also herein incorporated by reference in its entirety.

As disclosed above, the pharmacy tool is used to generate the drug library and/or to generate the run profile. The drug library generally includes a plurality of subdirectories, each of which is associated with one or more different drugs. In an example, each subdirectory is labeled with a care area, drug(s) that will be used, a mode of operation for infusing the drug(s), and data associated with the drug(s) to be infused. Further details of the drug library may be found in commonly-owed U.S. Patent Provisional Application Ser. No. 61/198,683, which is herein incorporated by reference in its entirety.

Figure 2:
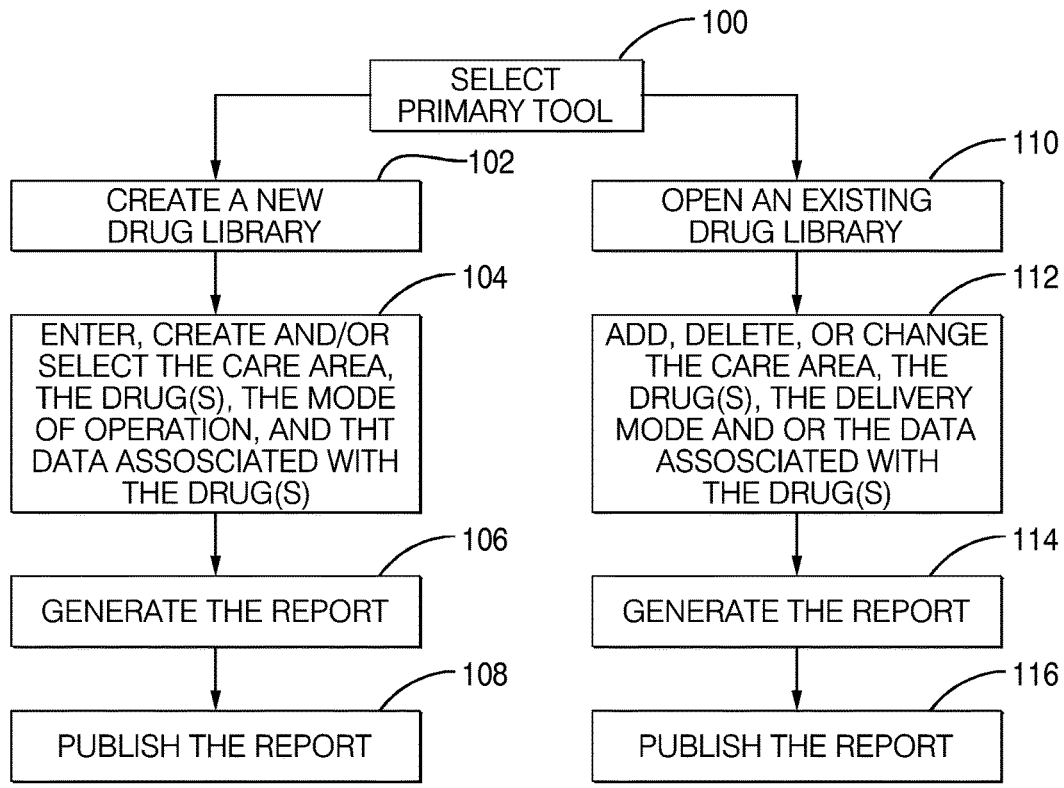
FIG. 2 is a flow diagram schematically depicting an example of a tool for generating a master drug library.

Referring now to FIG. 2, to generate the drug library, the user selects a pharmacy tool option from an introductory menu of the main tool to execute the pharmacy tool (as shown by reference numeral 100) and then selects to create a new drug library (as shown by reference numeral 102). When the user creates a new drug library, the user will enter, create, and/or select the care area, the drug(s), the mode of operation for infusing the drug(s), and the data associated with the drug(s) to be infused (as shown by reference numeral 104).

In an example, the user selects the care area from a list of care areas presented to the user from a drop-down box in the pharmacy tool. If, for example, a desired care area is not provided in the list of care areas, the user may otherwise create the desired care area by entering the desired care area into the pharmacy tool. In some instances, the desired care area that is newly created is saved in the list of care areas for future use.

In another example, the user selects a drug from a list of drugs presented to the user from another drop-down box in the pharmacy tool. If, for example, a particular drug is not provided in the list, the user may otherwise create the drug by entering the drug name into the pharmacy tool. It is to be understood that the drug name identifies the drug by either i) a chemical name of the main ingredient of the drug, or ii) a trademarked name. Once the drug has been created, the newly created drug may be saved in the list of drugs in the pharmacy tool for future use.

In some instances, the user may want to delete one or more care areas or drugs from their respective lists in the pharmacy tool. This may be accomplished by selecting the care area or the drug from their respective lists and executing a delete function. In a non-limiting example, the delete function may be executed by selecting a "Delete" icon presented on the screen, by hitting the "Delete" key on the computer keyboard, executing a right-click function on the mouse and selecting a "Delete" option, or the like.

In yet another example, the user selects the mode of operation (also referred to herein as the delivery mode) from a list of delivery modes presented to the user in the pharmacy tool. In some instances, each delivery mode may be presented to the user with an adjacent checkbox. In other instances, the delivery modes may be presented to the user via a drop-down box. It is to be understood that, in some instances, a drug selected or created by the user cannot be infused via one or more of the delivery modes presented to the user. The pharmacy tool is programmed to recognize such instances and freeze out the appropriate delivery mode(s) by, e.g., whiting-out the delivery mode option so that it cannot be selected via a mouse click or checked if a checkbox is present.

In still another example, the user enters the data associated with the drug(s) into the pharmacy tool. The data may be, for example, a concentration of the drug(s) and/or other infusion parameters associated with and dependent upon the drug. Non-limiting examples of the infusion parameters include maximum and minimum hard limits of the volume of the drug to be infused, maximum and minimum soft limits of the volume of the drug to be infused, maximum and minimum hard limits of the dose rate, maximum and minimum soft limits of the dose rate, or combinations thereof. Units for the concentration and the infusion parameters may be selected from a list of units provided in the pharmacy tool. In some instances, a minimum delay time for infusing the drug may also be inputted into the pharmacy tool.

It may, in some instances, be important to include medical or technical information regarding the drug such as, e.g., warnings, possible side effects, compatibility of the drug with another drug, and/or the like. It may also be important, for some drugs, to include suggestions for infusing the drug (e.g., dosages, duration, etc.). Such information may be inputted in an advisory box presented to the user when using the pharmacy tool. When the drug library is published (which will be described in further detail below), the information will be included therein.

After the care area, the drug, the delivery mode, and the data associated with the drug has been entered, created, and/or selected by the user, a report may be generated (as shown by reference numeral 106). In an embodiment, the report includes the foregoing information entered, created, and/or selected by the user using the pharmacy tool organized in a manner suitable for the drug library.

In an embodiment, a completeness check may be performed, where the pharmacy tool checks that all of the necessary information has been selected, created and/or entered by the user prior to generating the report. If any information is missing, the user may, e.g., be prompted to enter the necessary information prior to generating the report.

After generating the report, the user may select to publish the report (as shown by reference numeral 108). The published report is a non-editable version of the master drug library, which is saved in the computer.

As referred to above, the published version of report (i.e., the master drug library) cannot be edited and re-saved as the same version of the master drug library. It is to be understood that to add, remove, and/or otherwise change any of the subdirectories of the master drug library, a new version of the drug library must be created. The new version of the master drug library may be created by selecting, in the pharmacy tool, to open an existing drug library saved in the computer (as shown by reference numeral 110 in FIG. 2).

This may be accomplished by retrieving a desired version of the master drug library from a bank of drug libraries saved in the computer. The user may then edit, using the pharmacy tool, the desired version of the drug library by adding, deleting, and/or otherwise changing at least one of the care area, the drug(s), the delivery mode, and/or at the data associated with the drug (as shown by reference numeral 112). The user may then select to generate a report of the edited version of the retrieved drug library (as shown by reference numeral 114). If no other changes are necessary and/or desirable, the report may be published and saved in the computer as another version of the master drug library (as shown by reference numeral 116).

As also disclosed above, the pharmacy tool may be used to create a run profile (also referred to herein as a barcode label including at least an infusion protocol) for the infusion pump. In an example, the information used for creating the run profile is retrieved from a physician's prescription for a patient and the run profile is created by the pharmacy.

Figure 3:
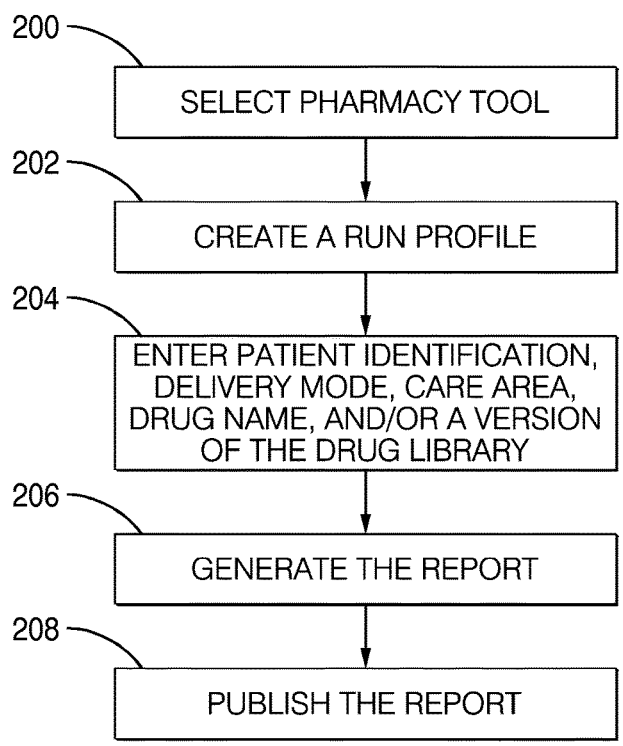
FIG. 3 is a flow diagram schematically depicting an example of a tool for generating a run profile.

Referring now to FIG. 3, creating the run profile may be accomplished by selecting the pharmacy tool option from the introductory menu of the main tool (as shown by reference numeral 200) and then selecting to create a run profile (as shown by reference numeral 202). When the user creates the run profile, the user enters a patient identification, a delivery mode, a care area, a drug name, and/or a version of the drug library (as shown by reference numeral 204). The version of the drug library is included in the run profile to check that the version of the drug library currently on the pump 12 matches the version used when creating the run profile. In some instances, other infusion parameters and/or instructions for infusing the drug that, in some instances, is specific to the patient may also be entered into the pharmacy tool.

After entering, into the pharmacy tool, the patient's identification, the delivery mode, the care area, the drug name, and/or the version of the drug library, a machine-readable label (e.g., a barcode label) is generated (as shown by reference numeral 206). In an embodiment, the machine-readable label is the machine-readable label 36, which is ultimately affixed to the drug container 34 (shown in FIG. 1). As described in further detail in U.S. Patent Provisional Application Ser. No. 61/198,681 , (referenced above), information included in the machine-readable label 36 is inputted into the infusion pump 12 by scanning the machine-readable label 36 with the machine-readable scanner 24 associated with the infusion pump 12.

To reiterate from above, the biotech tool is used to configure the infusion pump 12 and includes a plurality of sub-tools such as a device configuration tool, a write-to-the-pump tool, a reporting and commands tool, a software update tool, a logging tool, and an certification tool. Any one of these tools may be selected from a sub-tool menu presented to the user after the user has selected the biotech tool from the introductory menu of the main tool.

The device configuration tool generally allows the user to enable/disable one or more functions of the infusion pump 12 and/or to preset certain operating parameters for the pump 12. All possible pump settings are presented to the user under the device configuration tool. These pump settings are presented to the user in categories, non-limiting examples of which include infusion parameters (e.g., bolus, concentration, etc.), identification of the patient, delivery mode, power-saving configuration, miscellaneous items, and/or the like. Under each category is a number of different options, including a description for each option if highlighted by the user (via, e.g., a mouse click) that the user may enable/disable or preset.

In an example, the pump settings may be inputted into the biotech tool by i) manually inputting the presets and/or manually enabling/disabling one or more of the options, ii) reading the pump settings from default settings of the infusion pump 12 (generally pre-established by the pump manufacturer), iii) reading the pump settings from the infusion pump 12 itself, or iv) reading the pump settings from a file either saved on the computer running the main tool, from a portable memory device, or retrieved from another computer via a network. It is to be understood that an appropriate communication path between the computer running the main tool and the infusion pump is necessary if the pump settings are read from default settings of the pump or from the pump itself.

The write-to-the-pump tool is generally used to load the pump settings determined from the device configuration tool into the infusion pump. This may be accomplished by transmitting the pump settings from the computer running the main tool to the infusion pump 12 after establishing an appropriate communication path between them. In an example, an authorized user of the biotech tool may edit one or more of the pump settings as he/she deems appropriate (such as to customize the pump 12 for a particular care area or to perform a particular function). These edited settings are saved on the computer running the tool and transmitted to the pump. It is to be understood that the write-to-the-pump tool is also useful for loading pump settings to more than one pump, especially when the pump settings are different for each pump.

The reporting and commands tool is generally used to allow a user of the main tool to operate various functions of the pump 12 and/or to read internal variables of the pump 12 while the pump 12 is operating. For example, if an error or problem occurs with the pump 12 during its operation, the user of the main tool, through the reporting and commands tool, can trouble shoot the error or problem by allowing the user of the main tool to review the internal variables of the pump 12 while the pump 12 is operating. In another example, if no errors or problems with the pump 12 are currently evident, the user of the main tool may request, from the infusion pump 12, a report including one or more operating parameters of the pump 12 during an infusion. After reviewing the report, the user may command the infusion pump 12, using the reporting and commands tool, to perform various functions suitable to operate the infusion pump 12. Further, the commands may be used as part of the certification tool, described in further details below.

The software update tool is used to allow the user of the main tool to update any software on the pump 12 including, for example, the drug library, main controller software, motor controller software, and/or the like. For example, the drug library generated by the pharmacy tool may be downloaded to a number of pumps in order to update the pumps with a current version of the drug library. Additionally, software updates for the main controller and/or the motor controller are downloaded to the pumps from, e.g., their respective manufacturers. The software updates allow, for example, i) new functions to be added to the pumps, and/or ii) existing functions on the pump to be corrected, expanded, and/or removed. Downloading may be accomplished using a suitable communications link (e.g., a wired connection, Zigbee®, Wi-Fi, or the like).

The logging tool generally allows the user to download report(s) from the pump 12 and to record the report(s) on the computer running the main tool. In an example, the user may generate i) a general report (also referred to herein as a log) including data related to an operation of the pump, ii) a patient-controlled analgesia (PCA) log including data related to a PCA delivery of a drug via the pump, iii) an alarm log including data related to an alarm condition of the pump, and/or iv) a patient information log including data related to the patient. These logs may be used for future review of the pump 12 regarding its history of use, the patient, and/or the infusion protocol followed during a particular infusion of a drug to the patient.

The certification tool allows a user of the main tool to check (for example, annually) one or more functionalities of the pump 12 and/or to certify that the pump 12 is performing to predetermined standards and specifications. The certification tool may be used to check, for example, an operation state of the infusion pump, an operation state of components associated with the infusion pump, and/or maintenance of the infusion pump. In a non-limiting example, the certification tool is used to check: if the pump and/or pump head has/have been cleaned; software status; a battery; sensor(s); if various functions of the pump 12 are working properly; the flow of fluid traveling through the tube 32; a real time clock; an alarm; the safety of the pump 12; set next maintenance date; update reports and/or files for the biotech tool; and/or the like, and/or combinations thereof. The certification check may be accomplished periodically (e.g., weekly, monthly, annually, or another other suitable time frame).

To reiterate from above, in an embodiment, the main tool further includes a tool for configuring the main tool for a user. This tool is referred to herein as the administrator tool. In an example the administrator tool is used to setup and/or configure the main tool for an appropriate user. In another example, the administrator tool is used to configure the main tool for several appropriate users. In yet another example, the appropriate user(s) is/are authorized users. In an embodiment, the administrator tool configures the main tool by i) adding and/or deleting a user (including assigning a user identification, which allows the user to log into the main tool), ii) assign access rights to the user for the pharmacy tool, the biotech tool, or both, and iii) apply updates to the main tool. In another embodiment, the administrator tool is also used to initially install and set up the main tool by a user who has administrative privileges to do so.

While several embodiments have been described in detail, it will be apparent to those skilled in the art that the disclosed embodiments may be modified. Therefore, the foregoing description is to be considered exemplary rather than limiting.

What is claimed is:

1. An infusion pump system, comprising:
an infusion pump; and
an apparatus for interfacing with the infusion pump, the apparatus including:
a pharmacy tool including a drug library of a plurality of drugs, the drug library including information regarding name, concentration, and delivery mode of each of the plurality of drugs, the pharmacy tool being configured to update the drug library according to a user input and assign a version identifier to each update of the drug library, each update associated with a change to the information of the plurality of drugs, the pharmacy tool configured to generate a run profile from a retrieved physician's prescription for a patient, the run profile corresponding to an infusion protocol of one of the plurality of drugs of the drug library on the infusion pump for the patient;
a machine readable label generator configured to generate a machine readable label that includes the run profile and the version identifier of the drug library on the pharmacy tool associated with the run profile; and
a biotech tool adapted to configure the infusion pump, including sending the drug library and the version identifier to the infusion pump for local storage on the infusion pump;
wherein the infusion pump is configured to determine whether the version identifier on the generated machine readable label matches the version identifier sent from the biotech tool, and perform an action based upon the determination that the version identifier sent from the biotech tool does not match the version identifier on the generated machine readable label;
wherein the infusion pump is configured to determine whether the run profile is within a safety standard;
wherein the action is an update of the drug library on the infusion pump via the pharmacy tool.

2. The system of claim 1, wherein configuring the infusion pump includes entering: at least one infusion parameter; an identification of the patient; a delivery mode; a power-saving configuration; or combinations thereof.

3. The system of claim 2 wherein configuring the infusion pump further includes:
requesting, from the infusion pump, a report including at least one operating parameter of the infusion pump during an infusion; and
commanding the infusion pump to perform functions suitable to operate the infusion pump.

4. The system of claim 2 wherein configuring the infusion pump further includes generating at least one of i) a general log including data related to an operation of the infusion pump, ii) a PCA log including data related to a PCA delivery of a drug using the infusion pump, iii) an alarm log including data related an alarm condition of the infusion pump, or iv) a patient information log including data related to the patient.

5. The system of claim 2 wherein the configuring the infusion pump further includes periodically checking at least one of: an operation state of the infusion pump; an operation state of components associated with the infusion pump; or maintenance of the infusion pump.

6. The system of claim 1, further comprising a certification tool configured to determine whether maintenance has been performed on the infusion pump.

7. The system of claim 6, wherein the maintenance includes a determination that the infusion pump has been cleaned.

8. The system of claim 6, wherein the certification tool includes determining a next maintenance date for maintenance on the infusion pump.

9. The system of claim 1, wherein the drug library includes a care area, at least one infusion parameter, and a report.

10. The system of claim 9, wherein the pharmacy tool is configured to publish the drug library.

11. The system of claim 1, wherein the run profile includes:
at least one of: a patient identification, a delivery mode, a care area, or a drug name.

12. The system of claim 1, wherein the machine readable label is a barcode label.

* * * * *